(12) United States Patent
Klassen

(10) Patent No.: US 7,179,480 B2
(45) Date of Patent: Feb. 20, 2007

(54) SUSTAINED RELEASE MICROCAPSULES

(75) Inventor: Darryl F. Klassen, London (CA)

(73) Assignee: 3M Innovative Properties Company, St. Paul, MN (US)

( * ) Notice: Subject to any disclaimer, the term of this patent is extended or adjusted under 35 U.S.C. 154(b) by 596 days.

(21) Appl. No.: 10/132,634

(22) Filed: Apr. 24, 2002

(65) Prior Publication Data
US 2003/0202999 A1 Oct. 30, 2003

(51) Int. Cl.
*A01N 25/28* (2006.01)

(52) U.S. Cl. .................. 424/417; 424/405; 424/406; 424/408; 424/409; 424/419; 514/549; 514/675; 514/703; 514/722; 514/739

(58) Field of Classification Search .................. 424/84, 424/400, 497, 489, 87, 451, 408, 417, 490–502
See application file for complete search history.

(56) References Cited

U.S. PATENT DOCUMENTS

| | | | |
|---|---|---|---|
| 3,429,827 A | | 2/1969 | Ruus |
| 3,577,515 A | * | 5/1971 | Vandegaer ............... 424/497 |
| 3,984,541 A | | 10/1976 | Letchworth et al. |
| 4,056,610 A | * | 11/1977 | Barber et al. ............ 424/419 |
| 4,323,556 A | | 4/1982 | Dal Moro et al. |
| 4,487,759 A | * | 12/1984 | Nesbitt et al. ............ 424/497 |
| 5,364,969 A | | 11/1994 | Sakurada et al. |
| 6,248,364 B1 | * | 6/2001 | Sengupta et al. ........ 424/501 |
| 6,540,991 B2 | * | 4/2003 | Klassen et al. ............. 424/84 |

FOREIGN PATENT DOCUMENTS

| | | |
|---|---|---|
| CA | 1044134 | 12/1978 |
| CA | 1 160 050 | 1/1984 |
| EP | 0 463 835 B1 | 2/1996 |
| GB | 1 513 614 | 6/1978 |
| JP | 63-51121 | 10/1988 |
| JP | 4-164004 | 6/1992 |
| JP | 5000909 A | 1/1993 |
| WO | WO 98/18830 | 5/1998 |
| WO | WO 00/25731 | 5/2000 |

OTHER PUBLICATIONS

Ideses et al., "Chemical Protection of Pheromones Containing an Internal Conjugated Diene System From Isomerization and Oxidation", Journal of Chemical Ecology, 1988, pp. 1657-1669, vol. 14, No. 8.
Millar, "Degradation and Stabilization of E8,E10-Dodecadienol, the Major Component of the Sex Pheromone of the Codling Moth (Lepidoptera: Tortricidae)", Journal of Economic Entomology, Oct. 1995, pp. 1425-1432, vol. 88, No. 5.
U.S. Appl. No. 09/425,636, filed Oct. 22, 1999, Active Material Within Hydrogel Microbeads.
U.S. Appl. No. 09/828,040, filed Apr. 6, 2001, Stabilized Active Materials.

* cited by examiner

*Primary Examiner*—Neil S. Levy
(74) *Attorney, Agent, or Firm*—Lisa P. Fulton

(57) ABSTRACT

A sustained release microcapsule comprises (a) an interfacially-polymerized polymer shell comprising at least one shell stabilizer; and (b) a fill composition comprising (1) at least one semiochemical and (2) at least one fill stabilizer.

21 Claims, 1 Drawing Sheet

SUSTAINED RELEASE MICROCAPSULES

FIELD

This invention relates to microcapsules containing biologically-active material, to compositions comprising the microcapsules, and to methods for preparing and using the microcapsules.

BACKGROUND

The use of insect mating disruption (MD) technology is an important component of the modern approach to pest regulation known as integrated pest management (IPM), which combines biological, cultural, physical, and chemical techniques to regulate pest populations while minimizing cost and environmental disturbances. The typical MD technique confuses male insects with pheromones from the natural chemical blends of conspecific females. Sources of sex pheromone are placed in a crop or environment at concentrations sufficient to hide the presence of females. The population of the next generation of larva is thus decreased, as well as the potential for future crop or environmental damage.

Due to regulatory and environmental pressures, insect pest control is moving away from exclusive reliance on organophosphate insecticides. As a result, alternative crop protection strategies, including pheromone MD technology, have steadily increased in general acceptance. Many pheromone MD products are point source dispensers and must be hand applied within the intended environment. Alternatively, sprayable MD products are available, but have generally been thought to suffer from too short a lifetime in commercial applications. The pheromones are often released and dissipate into the environment too quickly to provide effective mating disruption throughout an entire mating cycle of an insect pest, which may last up to 4 to 6 weeks.

SUMMARY

In view of the foregoing, we recognize that there is a need for microcapsules that can be used in sprayable pheromone MD products and that can provide sustained release of pheromone throughout an entire mating cycle of an insect pest, or longer.

Briefly, in one aspect, the present invention provides sustained release microcapsules. The microcapsules comprise (a) an interfacially-polymerized polymer shell comprising at least one shell stabilizer; and (b) a fill composition comprising (1) at least one semiochemical and (2) at least one fill stabilizer. As used herein, the term "stabilizer" means a substance capable of imparting resistance against physical or chemical deterioration or decomposition and the term "semiochemical" means a chemical that conveys a signal from one organism to another, for example, in such a way as to modify the behavior of the recipient organism (including, for example, allomones, kairomones, synomones, and pheromones, which can have, for example, arrestant, attractant, repellent, deterrent, or stimulant properties).

It has been discovered that the above-described microcapsules exhibit surprising longevity. The shell stabilizer/fill stabilizer combination used in the microcapsules of the invention is surprisingly effective at stabilizing the microcapsule such that a sustained release of the semiochemical can be maintained over time. The combination appears to exhibit a synergistic stabilizing effect, in that a far greater stabilizing effect is observed when both a shell stabilizer and a fill stabilizer are used than the sum of the effects of each used alone.

The microcapsules of the invention provide increased resistance to photodegradation and environmental weathering and are therefore particularly suitable for use in pheromone MD products. By protecting both the pheromone molecule and the polymer shell, the synergistic shell stabilizer/fill stabilizer combination greatly extends the longevity of pheromone microcapsules under direct ultraviolet (UV) irradiation so that a slow release of pheromone can be maintained throughout an insect pest's mating cycle. Furthermore, the microcapsules of the invention can be used in sprayable MD compositions. Thus, the microcapsules of the invention fill the need in the art for microcapsules that can be used in sprayable pheromone MD products that can provide effective protection throughout an entire mating cycle of an insect pest, thereby providing a more environmentally friendly method of pest management.

In other aspects, this invention also provides sprayable compositions comprising the microcapsules of the invention; a method for making the microcapsules; and a method for using the microcapsules to control insect pest activity.

BRIEF DESCRIPTION OF THE DRAWING

These and other features, aspects, and advantages of the present invention will become better understood with regard to the following description, claims, and accompanying drawing, wherein:

DETAILED DESCRIPTION

Stabilizers

Figure 1:
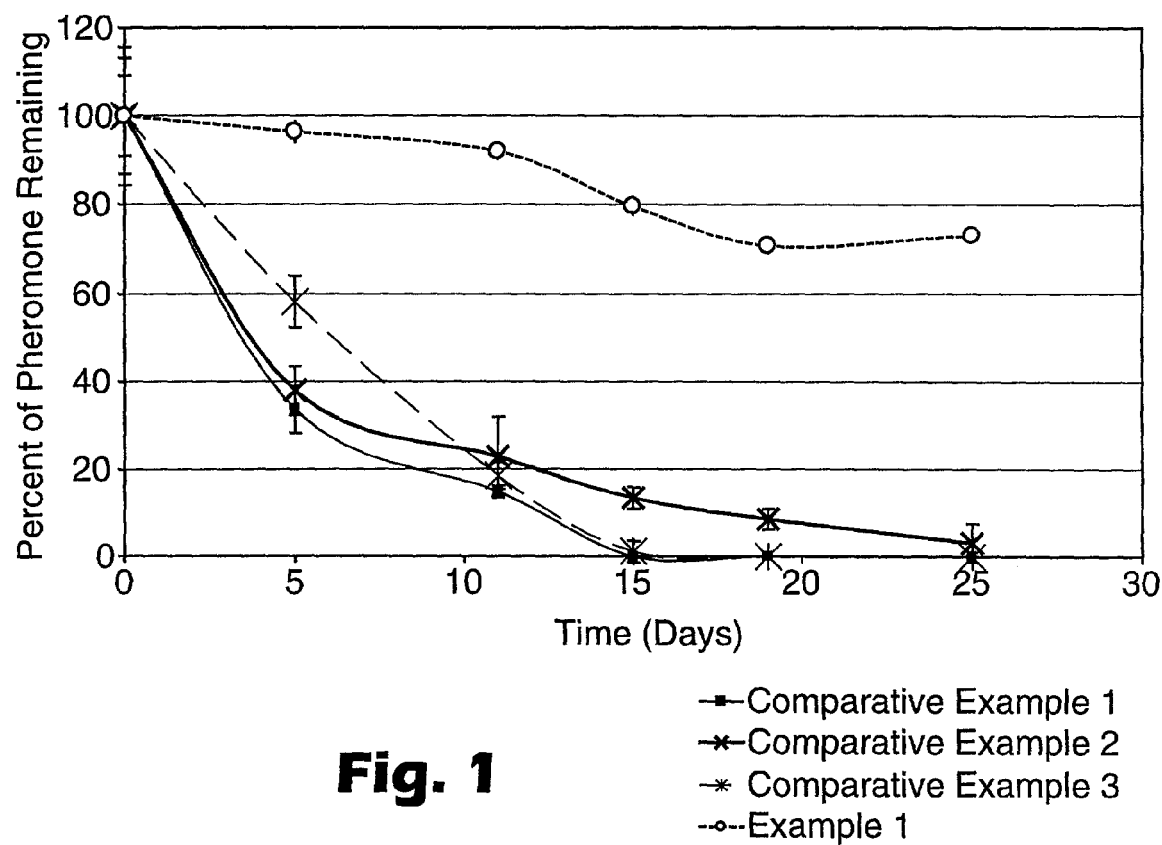
FIG. 1 is a plot of percent pheromone remaining versus time for a series of microcapsules described in Comparative Examples 1–3 and Example 1, infra.

The polymer shell and the fill composition of the microcapsules of the invention each comprise at least one stabilizer. Stabilizers that can be used in the polymer shell (referred to herein as "shell stabilizers") and stabilizers that can be used in the fill composition (referred to herein as "fill stabilizers") include, for example, antioxidants and thermal stabilizers, and ultraviolet (UV) absorbers (preferably, antioxidants and UV absorbers). Preferred shell stabilizers are those that comprise reactive groups that enable covalent incorporation into the polymer shell. Such stabilizers can comprise, for example, one or more reactive groups such as amine, hydroxyl, phosphine, sulfur, vinyl, epoxy, isocyanate, acid halide, anhydride, reactive esters, or other similar groups.

Antioxidants and thermal stabilizers minimize the degradative effects of mechanical, thermal, photoinduced, and auto-catalytic degradation processes. When used in the microcapsules of the invention, antioxidants can, for example, suppress, reduce, intercept, or eliminate destructive radicals or chemical species that promote the formation of destructive radicals that would otherwise lead to more rapid degradation of the microcapsule fill, shell, or both. Antioxidants that are suitable for use as shell stabilizers and fill stabilizers include, for example, sterically hindered phenols, bisphenols, aminophenols, secondary aromatic amines, hydroxybenzyl compounds, alkyl and arylthioethers, thiobisphenols, phosphates and phosphonites, zinc-thiocarbamates, benzofuranone lactone-based antioxidants, nickel quenchers, metal deactivators or complexing agents, hindered amine light stabilizers (HALS), and the like.

Representative examples of suitable antioxidants and/or thermal stabilizers include butylated hydroxyanisole (BHA), 2,6-di-t-butyl cresol (BHT), 2,2'-methylene bis(6-t-butyl-4-methyl phenol)(available as Vulkanox™ BKF from Bayer Inc., Canada), 2,2'-thio bis(6-t-butyl-4-methyl phenol), tert-butyl hydroquinone, di-tert-butyl hydroquinone, di-tert-amyl hydroquinone, methyl hydroquinone, p-methoxy phenol, tetrakis[methylene-3-(3',5'-di-tert-butyl-4'-hydroxyphenyl)propionate]methane, N-(2-aminoethyl)-3-[3,5-bis(tert-butyl)-4-hydroxyphenyl]propanamide, 5,7-di-tert-butyl-3-(3,4,-dimethylphenyl)-3H-benzofuran-2-one, dilauryl thiodipropionate, dimyristyl thiodipropionate, tris(nonylphenyl) phosphite, and the like, and mixtures thereof. These antioxidants are commercially available.

Preferred antioxidants and/or thermal stabilizers include, for example, butylated hydroxyanisole (BHA), 2,6-di-t-butyl cresol (BHT), 2,2'-methylene bis(6-t-butyl-4-methyl phenol)(Vulkanox™ BKF), di-tert-amyl hydroquinone, and N-(2-aminoethyl)-3-[3,5-bis(tert-butyl)-4-hydroxyphenyl] propanamide, and mixtures thereof; more preferred are 2,2'-methylene bis(6-t-butyl-4-methyl phenol) and N-(2-aminoethyl)-3-[3,5-bis(tert-butyl)-4-hydroxyphenyl]propanamide, the latter being particularly preferred as a shell stabilizer because it comprises a reactive amino group that enables covalent incorporation into the polymer shell.

UV absorbers that are suitable for use as shell stabilizers and fill stabilizers protect the microcapsule by absorbing radiation in the range of about 270–500 nanometers and subsequently releasing the energy into the environment through non-destructive means. Suitable UV absorbers include, for example, hindered amine light stabilizers (HALS), cinnamate esters, hydroxybenzophenones, benzotriazoles, substituted acrylates, salicylates, oxanilides, hydroxyphenyltriazines, and the like.

Representative examples of suitable UV absorbers include 2,4-dihydroxy benzophenone, 2-hydroxy-4-methoxy benzophenone, 2-hydroxy-4-octyloxy benzophenone (available as Chimassorb™ 81 from Ciba Specialty Chemicals, Canada), 2-(2'-hydroxy-3',5'-tert-amylphenyl)benzotriazole (available as Tinuvin™ 328 from Ciba Specialty Chemicals, Canada), 2-(2'-hydroxy-3'-tert-butyl-5'-methylphenyl)-5-chloro-benzotriazole (Tinuvin™ 326), 2-(2'-hydroxy-3',5'-di-tert-butylphenyl)-5-chloro-benzotriazole (Tinuvin™ 327), 2-(2'-hydroxy-5'-methylphenyl)benzotriazole (Tinuvin™ P), 2-(3',5'-diallyl-2'-hydroxylphenyl)benzotriazole, ethyl 2-cyano-3,3-diphenyl acrylate, 2-ethylhexyl-2-cyano-3,3-diphenyl acetate, 5-butyl phenyl salicylate, 2-amino-5-chlorobenzophenone, and the like, and mixtures thereof. These UV absorbers are commercially available.

Preferred UV absorbers include, for example, 2-hydroxy-4-methoxy benzophenone, 2-hydroxy-4-octyloxy benzophenone, 2-(2'-hydroxy-3',5'-tert-amylphenyl)benzotriazole, 2-(2'-hydroxy-3'-tert-butyl-5'-methylphenyl)-5-chloro-benzotriazole, 2-amino-5-chlorobenzophenone, and mixtures thereof; more preferred are 2-(2'-hydroxy-3',5'-tert-amylphenyl)benzotriazole and 2-amino-5-chlorobenzophenone, the latter compound being particularly preferred as a shell stabilizer because it comprises a reactive amino group that enables covalent incorporation into the polymer shell.

UV blockers (for example, carbon black, iron oxide(s), or titanium dioxide) can also be used in combination with antioxidants, thermal stabilizers, and/or UV absorbers in the microcapsules of the invention.

Semiochemicals

Semiochemicals are chemicals that convey signals from one organism to another. Semiochemicals that are suitable for use in the fill composition of the microcapsules of the invention include allelochemicals (chemicals that convey signals that are significant to individuals of a species different from the source species, for example, allomones, kairomones, or synomones) and pheromones (compositions comprising at least one chemical compound that conveys signals that are significant to individuals of the same species).

Preferably the semiochemical is a pheromone (including naturally or synthetically produced pheromones and synthetic pheromone analogs); more preferably, the semiochemical is an insect pheromone.

In describing the structure of pheromones, the following notation is generally used: the type (E (trans) or Z(cis)) and position of the double bond or bonds are given first, the number of carbon atoms in the chain is given next and the nature of the end group is given last. To illustrate, the pheromone Z-10 C19 aldehyde has the following structure:

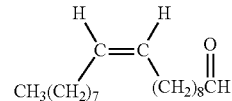

Pheromones can be mixtures of compounds with one component of the mixture predominating, or at least being a significant component. Predominant components of insect pheromones, with an example of a target species in parentheses, include, for example: E/Z-11 C14 aldehyde (Eastern Spruce Budworm), Z-10 C19 aldehyde (Yellow Headed Spruce Sawfly), E,E-8,10 C12 alcohol (Codling Moth), E-11 C14 alcohol/acetate (Tufted Apple Budmoth), E-11 C14 acetate (Sparganothis Fruitworm), Z-11 C14 acetate (Blackheaded Fireworm), Z-9 C12 acetate (Grape Berry Moth), Z-11 C14 acetate (Leafroller), E/Z-4 C13 acetate (Tomato Pinworm), Z,Z/Z,E-7,11 C16 acetate (Pink Cotton Bullworm), Z-8 C12 acetate (Oriental Fruit Moth), Z/Z-3,13 C18 acetate (Peach Tree Borer), E,Z/Z,Z-3,13 C18 acetate (Lesser Peach Tree Borer), E/Z-7 C14 2-ketone (Oriental Beetle), Z-6 C21 11-ketone (Douglas Fir Tussock Moth), and 7,8-epoxy-2-methyl C18 (Gypsy Moth), among others. Many of these pheromones are commercially available.

Preferred pheromones for use in the fill composition of the microcapsules of the invention include Z-11 C14 acetate (Leafroller) and Z-8 C12 acetate (Oriental Fruit Moth).

Shell Polymers

The microcapsules of the invention comprise an interfacially-polymerized polymer shell. Interfacial polymerization occurs when two reactant shell monomers contained in two immiscible liquids are brought together at the interface between the immiscible liquids and the interface becomes a reaction zone. Examples of polymers that can be produced by interfacial polymerization and that are suitable for use as the polymer shell in the microcapsules of the invention include polyamides, polysulfonamides, polyesters, polycarbonates, polyureas, polyurethanes, and copolymers thereof, and the like (preferably polyureas, polyamides, and copolymers thereof; more preferably, polyureas).

Many different pairs of shell monomers are capable of interfacial polymerization. An organic liquid can contain one or more condensation-polymerizable, oil-soluble or oil-dispersible monomers such as, for example, diacid chlorides, bischloroformates, disulfonyl chlorides, polyacid chlorides, polychloroformates, diisocyanates, polyisocyanates, polysulfonyl chlorides, phosgene, diacid anhydrides, cyclic carboxylic esters, lactams, sultones, or other similar materials. Water or aqueous liquid (for example, a blend of water and polar organic solvent) can contain one or more monomers capable of interfacially polymerizing with the condensation-polymerizable, oil-soluble or oil-dispersible monomer. For example, water or aqueous liquid can contain one, two, or more polyamines, polyols, or polyamine-ols (compounds having both amine and hydroxyl groups), or other similar materials having an average reactive group functionality of two or more. For instance, in the production of polyamide, an aqueous liquid containing polyamines can be mixed with an organic liquid containing polyacid chlorides.

Preferred shell monomer pairs for making polymers suitable for the polymer shell in the microcapsules of the invention include polyphenylmethane polyisocyanate/tetraethylenepentamine and sebacoyl chloride/hexanediamine.

Preparation of Microcapsules and Sprayable Compositions

The microcapsules of the invention can be made using an interfacial encapsulation method. The use of interfacial polymerization to encapsulate substances such as carbonless copy paper color formers, pesticides, and pheromones is well known in the art (see, for example, U.S. Pat. No. 3,429,827 (Ruus), U.S. Pat. No. 3,577,515 (Vandegaer), and U.S. Pat. No. 4,487,759 (Nesbitt et al.).

The novel method of the invention for making sustained release microcapsules comprises the steps of (a) preparing an organic phase comprising (1) at least one semiochemical, (2) at least one fill stabilizer, and (3) at least one condensation-polymerizable, oil-soluble or oil-dispersible monomer; (b) preparing an aqueous phase comprising at least one monomer capable of interfacially polymerizing with the condensation-polymerizable, oil-soluble or oil-dispersible monomer; (c) adding at least one shell stabilizer to the organic phase, to the aqueous phase, or to an optional separate aqueous phase; (d) dispersing the organic phase in an aqueous composition comprising at least one surfactant or colloidal stabilizer to form a dispersion; and (e) adding the aqueous phase and, if prepared, the optional separate aqueous phase to the dispersion.

Preferably, the shell stabilizer is capable of reacting with one or more of the shell monomers; more preferably capable of reacting with the condensation-polymerizable, oil-soluble or oil-dispersible monomer. Preferably, the shell stabilizer is added to the organic phase or to the optional separate aqueous phase. When the shell stabilizer is added to the optional separate aqueous phase, the aqueous phase and the optional separate aqueous phase can be added to the dispersion simultaneously or sequentially (preferably, they are added sequentially; more preferably, the optional separate aqueous phase is added to the dispersion before the aqueous phase is added).

Optionally, a gum phase comprising a suspension aid (for example, rhamsam gum, xanthan gum, gellan gum, pectin, or gum Arabic) can be added to the dispersion after capsule formation.

Shell stabilizers can either be blended (such that they become and remain part of the shell through physical or ionic interactions with the polymer) or can be covalently incorporated (through chemical reaction of one or more reactive groups of the shell monomer(s)).

The amounts of shell stabilizers and fill stabilizers can vary widely depending upon the nature of the components of the microcapsule and the intended environment. However, generally the microcapsules of the invention can contain at least about 0.01 weight percent shell stabilizer (preferably at least about 0.04 weight percent; more preferably at least about 0.08 weight percent) based upon the total weight of all components of the microcapsule. The amount of shell stabilizer can generally range up to about 2 weight percent (preferably up to about 0.3 weight percent; more preferably up to about 0.2 weight percent) based upon the total weight of all components of the microcapsule.

Generally the microcapsules of the invention can contain at least about 0.3 weight percent fill stabilizer (preferably at least about 1 weight percent; more preferably at least about 2 weight percent; most preferably at least about 5 weight percent) based upon the total weight of all components of the microcapsule. The amount of fill stabilizer can generally range up to about 70 weight percent (preferably up to about 40 weight percent; more preferably up to about 20 weight percent; most preferably up to about 10 weight percent) based upon the total weight of all components of the microcapsule.

The microcapsules of the invention can be used in sprayable compositions comprising at least one microcapsule of the invention and at least one diluent (preferably water). Generally, the sprayable composition can contain at least about 0.004 weight percent microcapsules based upon the total weight of the sprayable composition. The sprayable composition generally can contain up to about 80 weight percent microcapsules or more based upon the total weight of the sprayable composition.

Use of Microcapsules

It is possible to control insect pest activity by applying a composition comprising at least one microcapsule of the invention to an intended environment. The microcapsules of the invention gradually release the semiochemical contained in their fill composition over time. When the semiochemical is a pheromone, the microcapsules can be used to interfere with insect mating in intended environments such as, for example, fruit trees, vines, forests, vegetables, row crops, cotton, and the like.

The microcapsules of the invention can be delivered to the intended environment by methods known in the art. For example, they can be delivered by spraying (for example, by aerial spraying or using hand-held, knapsack, tractor-drawn, or vehicle-mounted sprayers) or by chemigation (for example, using conventional irrigation equipment). Preferably, they are delivered by spraying. Typically, the microcapsules of the invention can be applied to the intended environment such that the application rate of the active is about 0.1 to about 40 grams per acre.

EXAMPLES

Objects and advantages of this invention are further illustrated by the following examples, but the particular materials and amounts thereof recited in these examples, as well as other conditions and details, should not be construed to unduly limit this invention.

Aging Test Method

Oriental Fruit Moth (OFM) Pheromone Laboratory Blacklight Blue (UV) Aging—Sample Preparation and Exposure A sample frame (approx. 35.5 cm×35.3 cm) was constructed by securing four 35.5 cm×2.5 cm×0.6 cm (l.w.h.) pieces of wood together to form a square. One face of the square was covered with wire window screen material that was secured to the frame using a staple gun. Approximately 0.95 cm wide cork strips were secured to the frame at approx. 2.5 cm spacings.

Approximately 1.9 cm squares were cut from commercial "food use" wax paper. Rows of wax papers were secured to the wire face of the frame by inserting a pin through the edges of the wax paper square, through the screen and into the cork strip.

Samples of the microcapsules of the invention were diluted approximately 1:40 with deionized water in glass bottles. The resulting formulations were shaken thoroughly to mix, and 100 μL samples of formulation were applied to the wax paper squares. The sample frame was placed under a parallel array of six Blacklight Blue UV-A (General Electric F20T12/BLB) fluorescent light bulbs (7.6 cm spacings). The distance from the samples to the face of the light array was approximately 6.4 cm. For each sample set, 10 samples were collected for time t=0, with five replicates collected at each additional sampling day (t=5, 11, 15, 19 and 25 days). At collection time, samples were transferred to 15 mL polypropylene centrifuge tubes and were stored frozen until analysis.

Sample Analysis

Reagent ethanol (3 mL) and internal standard (ISTD) solution comprising decanol were added to all sample tubes of instrument calibrators and aged samples. Instrument calibrators were prepared by spiking accurate volumes of stock Oriental Fruit Moth (OFM) pheromone (Shin-Etsu, Japan) calibration standard into tubes containing the ethanol and ISTD. The stock calibration standard was prepared by accurately diluting neat OFM pheromone with reagent ethanol in a volumetric flask. Aged samples were sonicated for 30 minutes. Samples and calibrators were vortex mixed, and approximately 1.5 mL of samples were filtered through Kimwipe™ paper tissue (Kimberly-Clark) plugs in glass pipettes. All filtered samples and calibrators were transferred to vials and were analyzed by automated capillary gas chromatography (Varian Model 3600 GC/FID & 8100 Autosampler, Varian Inc., Canada).

The amount of pheromone was determined in each sample, based on multipoint ISTD-based calibration curves.

For each sample set, average results were calculated for each sample day. The average sample day results were multiplied by 100 and then divided by the result for time t=0 to convert to percent residual pheromone. The conversion to percent residual allows for a direct formulation-to-formulation comparison of formulation longevity.

Comparative Example 1 (No Stabilizer)

A 1L-jacketed reactor was charged with 260 g of tap water and 2.60 g of Disponil™ A3065 ethoxylated fatty alcohol surfactant (Cognis Corp., Canada) and stirred for 10 minutes. An organic phase was prepared separately by mixing 100.0 g of E/Z 8 dodecenyl acetate (available as OFM technical pheromone, Shin-Etsu, Japan), 41.50 g Miglyol™ 812 triglycerides (Sasol North America, USA), and 12.5 g Mondur™ MRS polyphenylmethane polyisocyanate (Bayer Inc., Canada). An aqueous phase was prepared separately by dissolving 3.75 g tetraethylenepentamine (Union Carbide, Canada) in 57.15 g of tap water. The organic phase was added to the reactor and emulsified at 1050 rpm for 2 minutes before adding the aqueous phase all at once. The resulting mixture was stirred for 45 minutes before heating the reactor to 60° C. over 1 hour. The reactor was held at 60° C. for three hours. A gum phase was prepared by mixing 93 parts tap water with 4.66 parts Proxel™ GXL comprising 1,2-benzisothiazolin-3-one (BIT) preservative (Avecia Inc., USA) and 2.33 parts Kelzan™ HP xanthan gum (CP Kelco, USA). The reactor was cooled to ambient temperature and 22.5 g of gum phase was added. The resulting microcapsules were aged and analyzed in accordance with the above-described Aging Test Method, and the results are shown in FIG. 1 below.

Comparative Example 2 (Fill Stabilizer Only)

A 1L-jacketed reactor was charged with 260 g of tap water and 2.60 g of Disponil™ A3065 surfactant and stirred 10 minutes. An organic phase was prepared separately by mixing 100.0 g of OFM technical pheromone, 31.50 g Miglyol™ 812 triglycerides, 5.0 g Tinuvin™ 328 (2-(2'-hydroxy-3',5'-tert-amylphenyl)benzotriazole, Ciba Specialty Chemicals, Canada), 5.0 g Vulkanox™ BKF (2,2'-methylene bis(6-t-butyl-4-methyl phenol), Bayer Inc., Canada) and 12.5 g Mondur™ MRS polyphenylmethane polyisocyanate. An aqueous phase was prepared separately by dissolving 3.75 g tetraethylenepentamine in 57.15 g of tap water. The organic phase was added to the reactor and emulsified at 1050 rpm for 2 minutes before adding the aqueous phase all at once. The resulting mixture was stirred for 45 minutes before heating the reactor to 60° C. over 1 hour. The reactor was held at 60° C. for three hours. A gum phase was prepared essentially as in Comparative Example 1. The reactor was cooled to ambient temperature and 22.5 g of gum phase was added. The resulting microcapsules were aged and analyzed in accordance with the above-described Aging Test Method, and the results are shown in FIG. 1.

Comparative Example 3 (Shell Stabilizer Only)

A 1L-jacketed reactor was charged with 260 g of tap water and 2.60 g of Disponil™ A3065 surfactant and stirred for 10 minutes. An organic phase was prepared separately by dissolving 0.0325 g of N-(2-aminoethyl)-3-[3,5-bis(tert-butyl)-4-hydroxyphenyl]propanamide (3M Canada Company, Canada) in 31.50 g Miglyol™ 812 triglycerides and adding 100.0 g of OFM technical pheromone and 12.5 g Mondur™ MRS polyphenylmethane polyisocyanate. An aqueous phase was prepared separately by dissolving 3.75 g tetraethylenepentamine in 57.15 g of tap water. The organic phase was added to the reactor and emulsified at 1050 rpm for 2 minutes before adding the aqueous phase all at once. The resulting mixture was stirred for 45 minutes before heating the reactor to 60° C. over 1 hour. The reactor was held at 60° C. for three hours. A gum phase was prepared essentially as in Comparative Example 1. The reactor was cooled to ambient temperature and 22.5 g of gum phase was added. The resulting microcapsules were aged and analyzed in accordance with the above-described Aging Test Method, and the results are shown in FIG. 1.

Example 1 (Fill Stabilizer and Shell Stabilizer)

A 1L-jacketed reactor was charged with 260 g of tap water and 2.60 g of Disponil™ A3065 surfactant and stirred for 10 minutes. An organic phase was prepared separately by dissolving 0.0325 g of N-(2-aminoethyl)-3-[3,5-bis(tert-butyl)-4-hydroxyphenyl]propanamide (3M Canada Company, Canada) in 31.50 g Miglyol™ 812 triglycerides and adding 100.0 g of OFM technical pheromone, 5.0 g Tinuvin™ 328, 5.0 g Vulkanox™ BKF, and 12.5 g Mondur™ MRS polyphenylmethane polyisocyanate. An aqueous phase was prepared separately by dissolving 3.75 g tetraethylenepentamine in 57.15 g of tap water. The organic phase was added to the reactor and emulsified at 1050 rpm for 2 minutes before adding the amine phase all at once. The resulting mixture was stirred for 45 minutes before heating the reactor to 60° C. over 1 hour. The reactor was held at 60° C. for three hours. A gum phase was prepared essentially as in Comparative Example 1. The reactor was cooled to ambient temperature and 22.5 g of gum phase,was added. The resulting microcapsules were aged and analyzed in accordance with the above-described Aging Test Method, and the results are shown in FIG. 1.

The complete disclosures of the publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

I claim:

1. A microcapsule comprising (a) an interfacially-polymerized polymer shell comprising at least one shell stabilizer, said shell stabilizer being an antioxidant covalently bonded to said polymer shell; and (b) a fill composition comprising (1) at least one pheromone and (2) at least one fill stabilizer comprising one or more antioxidants and one or more UV absorbers.

2. The microcapsule of claim 1 wherein said polymer is a polyurea or a polyamide.

3. The microcapsule of claim 1 wherein said polymer shell further comprises a UV absorber.

4. The microcapsule of claim 1 wherein said pheromone is an insect pheromone.

5. The microcapsule of claim 4 wherein said pheromone is selected from the group consisting of E/Z-11 C14 aldehyde (Eastern Spruce Budworm), Z-10 C19 aldehyde (Yellow Headed Spruce Sawfly), E,E-8,10 C12 alcohol (Codling Moth), E-11 C14 alcohol/acetate (Tufted Apple Budmoth), E-11 C14 acetate (Sparganothis Fruitworm), Z-11 C14 acetate (Blackheaded Fireworm), Z-9 C12 acetate (Grape Berry Moth), Z-11 C14 acetate (Leafroller), E/Z-4 C13 acetate (Tomato Pinworm), Z,Z/Z,E-7,11 C16 acetate (Pink Cotton Bullworm), Z-8 C12 acetate (Oriental Fruit Moth), Z/Z-3,13 C18 acetate (Peach Tree Borer), E,Z/Z,Z-3,13 C18 acetate (Lesser Peach Tree Borer), E/Z-7 C14 2-ketone (Oriental Beetle), Z-6 C21 11-ketone (Douglas Fir Tussock Moth), and 7,8-epoxy-2-methyl C18 (Gypsy Moth).

6. The microcapsule of claim 1 wherein said polymer shell comprises a polymer formed from one or more monomers selected from diacid chlorides, bischloroformates, disulfonyl chlorides, polyacid chlorides, polychloroformates, diisocyanates, polyisocyanates, polysulfonyl chlorides, phosgene, diacid anhydrides, cyclic carboxylic esters, lactams, sultones, polyamines, polyols, and polyamine-ols.

7. The microcapsule of claim 1 wherein said polymer shell comprises a polyamide, a polysulfonamide, a polyester, a polycarbonate, a polyurea, a polyurethane, or a copolymer thereof.

8. The microcapsule of claim 1 wherein said shell stabilizer comprises one or more reactive groups capable of covalently bonding to said polymer shell, the one or more reactive groups being selected from an amine group, a hydroxyl group, a phosphine group, a sulfur atom, a vinyl group, an epoxy group, an isocyanate group, an acid halide group, an anhydride group, and a reactive ester.

9. The microcapsule of claim 1 wherein said shell stabilizer is N-(2-aminoethyl)-3-[3,5-bis(tert-butyl)-4-hydroxyphenyl]propanamide.

10. A microcapsule comprising (a) a polymer shell comprising (i) a polyamide, a polysulfonamide, a polyester, a polycarbonate, a polyurea, a polyurethane, or a copolymer thereof, and (ii) at least one shell stabilizer, said shell stabilizer being an antioxidant covalently bonded to said polymer shell; and (b) a fill composition comprising (1) at least one pheromone and (2) at least one fill stabilizer comprising an antioxidant, an optional UV absorber, or a mixture thereof.

11. The microcapsule of claim 10 wherein said shell stabilizer comprises one or more antioxidants selected from 2,2'-methylene bis(6-t-butyl-4-methyl phenol); 2,2'-thio bis (6-t-butyl-4-methyl phenol); tert-butyl hydroquinone; di-tert-butyl hydroquinone; di-tert-amyl hydroquinone; methyl hydroquinone; tetrakis[methylene-3-(3',5'-di-tat-butyl-4'-hydroxy-phenyl)propionate]methane; N-(2-aminoethyl)-3-[3,5-bis(tert-butyl)-4-hydroxyphenyl]propan-amide; dilauryl thiodipropionate; dimyristyl thiodipropionate; and tris (nonylphenyl) phosphite.

12. The microcapsule of claim 10 wherein said shell stabilizer comprises N-(2-aminoethyl)-3-[3,5-bis(tert-butyl)-4-hydroxyphenyl]propanamide.

13. The microcapsule of claim 10 wherein said fill stabilizer comprises at least one antioxidant and at least one UV absorber.

14. A microcapsule comprising (a) a polyurea shell comprising at least one antioxidant, said antioxidant being covalently bonded to said polyurea shell; (b) a fill composition comprising (1) at least one pheromone and (2) at least one antioxidant and at least one UV absorber.

15. The microcapsule of claim 14 wherein said antioxidant of component (a) is N-(2-aminoethyl)-3-[3,5-bis(tert-butyl)-4-hydroxyphenyl]propanamide.

16. The microcapsule of claim 14 wherein said antioxidant of component (b) is 2,2'-methylene bis(6-t-butyl-4-methyl phenol) or 2,6-di-t-butyl cresol.

17. The microcapsule of claim 14 wherein said UV absorber is 2-(2'-hydroxy-3',5'-tert-amylphenyl)benzotriazole or 2-hydroxy-4-octyloxy benzophenone.

18. A sprayable composition comprising (a) at least one microcapsule of claim 1 or claim 14; and (b) at least one diluent.

19. The composition of claim 18 wherein said diluent is water.

20. A sprayable composition comprising (a) at least one microcapsule of claim 10, and (b) at least one diluent.

21. A method of controlling insect pest activity comprising applying a composition comprising at least one microcapsule of claim 1 or claim 14 to an intended environment.

* * * * *

UNITED STATES PATENT AND TRADEMARK OFFICE
CERTIFICATE OF CORRECTION

PATENT NO. : 7,179,480 B2  
APPLICATION NO. : 10/132634  
DATED : February 20, 2007  
INVENTOR(S) : Darryl F. Klassen It is certified that error appears in the above-identified patent and that said Letters Patent is hereby corrected as shown below:

<u>Column 9,</u>
Line 10, delete "phase,was" and insert in place thereof -- phase was --.

<u>Column 10,</u>
Line 25, delete "di-tat-butyl" and insert in place thereof -- di-tert-butyl --.
Line 39, after "shell;" insert -- and --.

Signed and Sealed this

Fifteenth Day of April, 2008

JON W. DUDAS
*Director of the United States Patent and Trademark Office*